US008877036B2

(12) United States Patent
Yunus et al.

(10) Patent No.: US 8,877,036 B2
(45) Date of Patent: Nov. 4, 2014

(54) SMART SENSOR SYSTEM USING AN ELECTROACTIVE POLYMER

(75) Inventors: Sami Yunus, Namur (BE); Patrick Bertrand, Louvain la Neuve (BE); Anne Attout, Fleurus (BE)

(73) Assignee: Universite Catholique de Louvain, Louvain la Neuve (BE)

( * ) Notice: Subject to any disclaimer, the term of this patent is extended or adjusted under 35 U.S.C. 154(b) by 199 days.

(21) Appl. No.: 13/520,074

(22) PCT Filed: Jun. 2, 2010

(86) PCT No.: PCT/EP2010/057753
§ 371 (c)(1),
(2), (4) Date: Jun. 29, 2012

(87) PCT Pub. No.: WO2011/082837
PCT Pub. Date: Jul. 14, 2011

(65) Prior Publication Data
US 2012/0298530 A1   Nov. 29, 2012

(30) Foreign Application Priority Data
Jan. 7, 2010 (EP) ...................................... 10150280

(51) Int. Cl.
*G01N 27/333* (2006.01)
*G01N 27/416* (2006.01)

(52) U.S. Cl.
CPC ........ *G01N 27/4161* (2013.01); *G01N 27/3335* (2013.01)
USPC .................... 205/787.5; 435/287.1; 422/68.1; 422/82.01; 204/416; 204/433; 204/406

(58) Field of Classification Search
CPC ........................... G01N 27/333; G01N 27/416

USPC ................................... 205/787.5, 777.5, 789; 204/403.01–403.15, 406, 416; 422/68.1, 82.01; 435/287.1
See application file for complete search history.

(56) References Cited

U.S. PATENT DOCUMENTS

2002/0070128 A1   6/2002   Beckmann
2004/0182719 A1   9/2004   Purvis

OTHER PUBLICATIONS

Poghossian et al. (Sensors and Actuators, B 78, 2001, 237-242).*
Gopinath et al. (Chem.Educator 2005).*
International Search Report for PCT/EP2010/057753 mailed Jul. 16, 2010 (7 pages).

(Continued)

*Primary Examiner* — Jennifer Dieterle
(74) *Attorney, Agent, or Firm* — Gardere Wynne Sewell LLP; Andre M. Szuwalski (57) ABSTRACT

A system for measuring a solution pH includes a potentiostat with a working electrode made of an electro-conductive solid polymer transducer, an input to receive the potential to be applied between the working electrode and a reference electrode, and an output to transmit a signal representative of the current flowing between a counter electrode and the working electrode, the three electrodes being immerged into the solution. The system further includes a digital processor connected to a digital to analog converter for generating the potential to be applied between the working and the reference electrodes; and to an analog to digital converter for receiving a digital value representative of the current. The digital processor is adapted to modify the potential to maintain the current inside a predetermined range such that the potential is representative of the solution pH when the current is inside the predetermined range.

18 Claims, 6 Drawing Sheets

(56) References Cited

OTHER PUBLICATIONS

Marylene Vandevenne, et al: "The *Bacillus licheniformis* BlaP β-lactamase as a model protein scaffold to study the insertion of protein fragments," Protein Science, Apr. 2, 2007, pp. 2260-2271.

Sami Yunus, et al: "Controlled Aniline Polymerization Strategies for Polyaniline Micro-and Nano Self-Assembling into Practical Electronic Devices," American Chemical Society, Jan. 6, 2009, pp. 1851-1854.

Chun-Yueh Huang, et al: "Design of a Portable Potentiostat for Electrochemical Sensors," IEEE Xplore, 2004, pp. 331-336.

Boris Lakard, et al: "Potentiometric miniaturized pH sensors based on polypyrrole films," Elsevier, Science Direct, Sensors and Actuators B 122 (2007), pp. 101-108.

Yang Jin, et al: "Reliable Remote-Monitoring Electrochemical Potentiostat for Glucose Measurements," Tsinghua Science and Technology, ISSN 1007-0214 Jul. 18 pp. 593-600, vol. 14, No. 5, Oct. 2009.

Gang Cui, et al.: "Potentiometric pCO2 sensor using polyaniline-coated pH-sensitive electrodes," The Analyst, Apr. 16, 1998, 123, pp. 1885-1859.

* cited by examiner

SMART SENSOR SYSTEM USING AN ELECTROACTIVE POLYMER

PRIORITY CLAIM

This application is a 371 filing from PCT/EP2010/057753 filed Jun. 2, 2010, which claims priority from European Application for Patent No. 10150280.5 filed Jan. 7, 2010, the disclosures of which are hereby incorporated by reference.

FIELD OF THE INVENTION

The invention relates to the field of system for measuring a solution pH comprising a potentiostat with a working electrode made of an electro-conductive solid polymer transducer.

BACKGROUND OF THE INVENTION

Sensors based on the electrochemical activity of an electro-conductive solid polymer transducer such as polyaniline (PANI) or polypyrrole are getting increased attention in the scientific community owing to their numerous advantages.

Polyaniline is a very convenient material when used as a solid electrochemical transducer owing to its many interesting intrinsic combinations of redox and acido-basic states. This polymer is known as stable and highly conductive in its emeraldine acid form.

Polyaniline also makes it possible to chemically, i.e. by chemical grafting, or physically, i.e. by physisorption, sensitize its surface with natural or engineered biochemical agents for biosensing purposes. As an example, some enzymes are well known to release protons from their specific substrate hydrolysis. This allows to develop sensors based on a proton releasing enzyme mediator.

In this context, the polyaniline protonation state strongly affects the equilibria between its redox states. This material can be electrochemically characterized to indicate the pH of an aqueous solution. Indeed, a simple potentiometry measurement of a polyaniline covered working electrode against a reference electrode displays a simple nernstian behavior as a function of the proton concentration. This simple system, similar to a conventional combined pH electrode, can be viewed as a battery cell having a limited charge and producing its own potential difference proportional to pH.

The two electrodes potentiometry measurements are passive: a constant discharging of the cell, through its internal resistance and through the high impedance measuring voltmeter, occurs. This can, in some cases, cause unwanted alteration of polyaniline redox states and cause a drift in the measured potentials. It is as though the reference and working electrodes were pulling each other's electrochemical potential to annul their difference by a small current exchange through the solution and the measuring instrument internal impedance. This drawback effect can be easily rendered negligible by using large surface working electrodes, thus increasing the available charge, but can however completely prevent reliable measurements at the micro and nano scales. Moreover, polyaniline electrochemical impedance varies simultaneously as a function of both the pH and its electrochemical potential.

For these reasons and for the sake of simplicity, electrochemical sensors, that are supposed to be used more than once or during long periods of time, favor the use of a continuous actuation during sensing rather than a supplementary differed protocol for electrochemical resetting or reloading. In an ideal active sensor, the actuation channel has to control, as best it can, some interface physico-chemical properties such as redox, acid-base and dielectric activities. This actuation is made in order to keep the transducer properties as unchanged as possible while observing at the same time how the system proceeds to do so in its feedback control. Moreover, in a sensor array, different actuations could lead to either increased selectivity or sensitivity or precision, starting from initially identical micro or nano-sensors.

A well-known equipment to investigate reaction mechanisms related to redox chemistry and other chemical phenomenon is the potentiostat. A potentiostat is a control and measuring device using three electrodes: a working electrode, a reference electrode and a counter electrode. A basic use of a potentiostat consists to consider it as an electric circuit which controls the potential across the cell by sensing changes in its impedance, varying accordingly the current supplied to the system: a higher impedance will result in a decreased current, while a lower impedance will result in an increased current, in order to keep the voltage constant. As a result, the variable system impedance and the controlled current are inversely proportional.

$$I_o = \frac{E_c}{R_v}$$

Where $I_o$ is the output electrical current of the potentiostat, $E_c$ is the input voltage that is kept constant and $R_v$ is the electrical impedance that varies.

Figure 1:
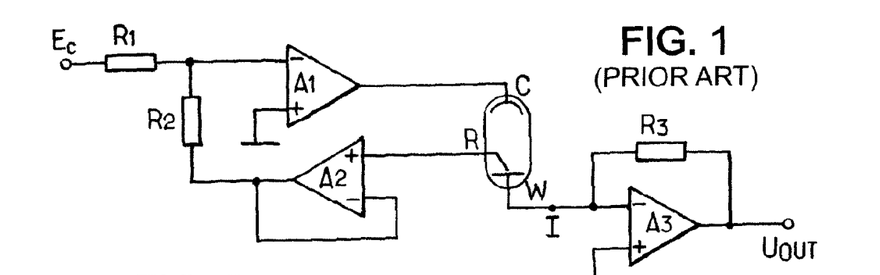
FIG. 1 is a schematic view of a potentiostat according to the prior art.

The potentiostat, FIG. 1, in its conventional architecture needs thus an input signal $E_c$, which is the difference in potential to be applied between the working electrode W and the reference electrode R. Then, the potentiostat generates an output signal $U_{out}$ that is proportional to the magnitude of the current flowing between the counter electrode C and the working electrode W. The current flow serves to maintain the working electrode W at the desired potential against the reference electrode's one. This system can be considered as the imbrications of operational amplifiers (Integrated Circuit, IC) into an analogue feedback loop. In the schema of FIG. 1, A1 is used as an adder, A2 as a voltage follower and A3 as a current to voltage converter scaled by a selected resistance R3.

SUMMARY OF THE INVENTION

It would be advantageous to achieve an apparatus for measuring solution pH with a potentiostat in which the drift of polyaniline working electrode is controlled to obtain reliable and repeatable measurements.

To better address one or more concerns, in a first aspect of the invention a system for measuring a pH solution comprises:

A potentiostat comprising a working electrode made of an electro-conductive solid polymer transducer, an input to receive an input signal indicative of the potential to be applied between the working electrode and a reference electrode of the potentiostat, and an output to transmit an output signal indicative of the magnitude of the current flowing between a counter electrode of the potentiostat and the working electrode, the three electrodes being immerged into the solution;

a digital processor connected to a digital to analog converter for generating the potentiostat input signal; and to an analog to digital converter for receiving a digital value representative of the potentiostat output signal.

The digital processor is adapted to modify the potentiostat input signal in order to maintain the output signal inside a predetermined range such that the input signal potential is representative of the solution pH when the output signal is inside the predetermined range.

In a particular embodiment:
the working electrode is made of polyaniline or polypyrrole;
the predetermined range is centered on zero;
the potentiostat comprises an operational amplifier having an input connected to the working electrode, the operational amplifier output generating the output signal and said operational amplifier being mounted in parallel with a resistance for acting as a current to voltage converter scaled by the resistance, the resistance being high or infinite to limit the current by saturation of the operational amplifier; and/or
the resistance is modified in a range avoiding saturation of the operational amplifier and the output signal predetermined range is external to zero such that the redox state of the electro-conductive solid polymer transducer is modified by a current flow.

Depending on the type of measurement, a particular embodiment may be preferred as easier to adapt or as giving a better result. Aspects of these particular embodiments may be combined or modified as appropriate or desired, however.

In a second aspect of the invention a system for sensing biological molecules comprises a system as here above, wherein the electro-conductive solid polymer transducer is sensitized by a proton releasing enzyme mediator.

In a particular embodiment the proton releasing enzyme mediator comprises a β-lactamase enzyme.

In a third aspect of the invention, a method measures a solution pH with a potentiostat, the potentiostat comprising a working electrode made of an electro-conductive solid polymer transducer, an input to receive an input signal indicative of the potential to be applied between the working electrode and a reference electrode of the potentiostat, and an output to transmit an output signal indicative of the magnitude of the current flowing between a counter electrode of the potentiostat and the working electrode, the three electrodes being immerged into said solution. The method comprises:
generating the input signal;
sensing the output signal;
modifying the input signal to maintain the output signal inside a predetermined range such that the input signal potential is representative of the solution pH when the output signal is inside the predetermined range.

In a fourth aspect of the invention, a computer software product stored on a recording media comprises a set of instructions to enable a computer to practice the here above method when the computer executes the set of instructions.

BRIEF DESCRIPTION OF THE DRAWINGS

These and other aspects of the invention will be apparent from and elucidated with reference to the embodiment described hereafter where:

FIGS. 6A, 6B and 6C are views of an array of micrometric interdigitated electrodes where

DETAILED DESCRIPTION OF THE DRAWINGS

Figure 2:
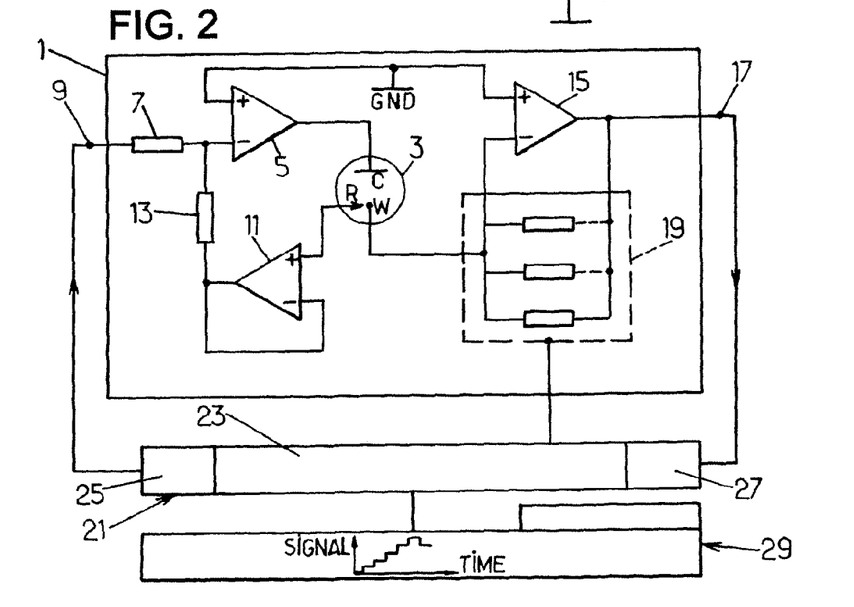
FIG. 2 is a schematic view of a system according to an embodiment of the invention.

In reference to FIG. 2, a potentiostat 1 comprises a cell 3 of three electrodes: a working electrode W, a reference electrode R and a counter electrode C.

The counter electrode C is connected to the output of an operational amplifier 5 of which one input is connected to ground and the second input is connected through a resistance 7 to an input connector 9. A second operational amplifier 11 has a first input connected to the reference electrode R and its second input connected to its output and, through a second resistance 13, to the second input of the first operational amplifier 5. The working electrode W is connected to a first input of a third operational amplifier 15, the second input of the third operational amplifier being connected to ground and its output being connected to output connector 17 of the potentiostat. A resistance selector 19, called hereafter a multiplexer, is connected in parallel of the third operational amplifier 15 to the working electrode W and the output connector 17.

A computer 21 comprises a digital processor 23 connected to a digital to analog converter DAC 25 and to an analog to digital converter ADC 27. The DAC is connected to the input connector 9 of the potentiostat 1 and the ADC to its output connector 17.

The computer 21 further comprises a data display 29.

The processor 23 defines an input signal value to be generated by the DAC 25 as an input signal of the potentiostat 1 which is the difference in potential to be applied between the working electrode W and the reference electrode R. Then, the potentiostat generates an output signal that is proportional to the magnitude of the current flowing between the counter electrode C, and the working electrode W. The current flow serves to maintain the working electrode at the desired potential. The first operational amplifier 5 is used as an adder, the second operational amplifier 11 as a voltage follower, and the third operational amplifier 15 as a current to voltage converter scaled by a selected resistance 19.

The computer 21 acts as a supplementary feedback loop between the input and the output of the potentiostat. The aim of this feedback loop is to maintain the output signal in a predetermined range by acting on the input signal. In this configuration the feedback loop has to regulate the applied working potential as a function of the measured current.

The processor can implement different algorithms allowing this feedback control. As an example in FIG. 3, the processor applies an arbitrary working potential $P_i$ on the potentiostat, step 31. This action will result in a current flow in the electrochemical $I_o$ measured at step 33. The applied working potential $P_i$ can then be increased or decreased with a constant value dS to iteratively approach a desired current flow $I_{oTar}$, step 35: if the current flow $I_o$ is above the desired value $I_{oTar}$, the potential $P_i$ is decreased by dS and if the current flow $I_o$ is less than the desired value $I_{oTar}$, the potential $P_i$ is increased by dS.

Figure 4:
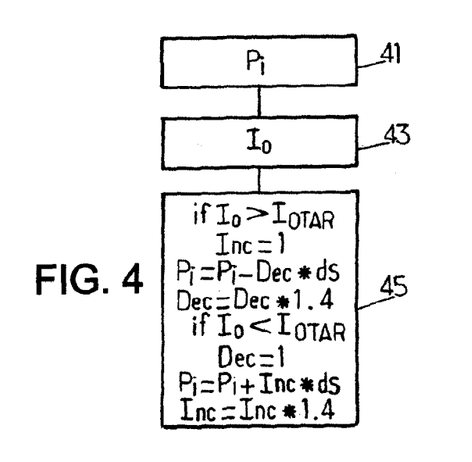
FIG. 4 is a flowchart of a second method of control of the system of FIG. 2.

The flowchart in FIG. 4 is a different algorithm consisting in variable increment or decrement steps for faster equilibrium settlement. The variable decrement/increment is defined as a multiple of 1.4. The processor applies an arbitrary working potential $P_i$ on the potentiostat, step 41. This action will result in a current flow in the electrochemical $I_o$ measured at step 43. The applied working potential $P_i$ can then be increased, or decreased with a variable value multiple of dS to iteratively approach a desired current flow $I_{oTar}$, step 45: if the current flow $I_o$ is above the desired value $I_{oTar}$, the increase factor Inc is reset to 1 and the potential $P_i$ is decreased by Dec*dS, then Dec is increased by a factor 1.4 and if the current flow $I_o$ is less than the desired value $I_{oTar}$, the decrease factor Dec is reset to 1 and the potential $P_i$ is increased by Inc*dS, then Inc is increased by a factor 1.4.

If an infinite resistor is selected in the multiplexer, the current to voltage converter 15 will saturate and limit the current between the counter and the working electrodes to the operational amplifier intrinsic current leak, i.e. typically 10 to 100 pA for common operational amplifiers. The current to voltage converter 15 will then reach a quasi infinite gain and will just mostly give two extreme values indicating if the applied potential is higher or lower than the polyaniline working electrode equilibrium potential. In this configuration, with $I_{oTar}=0$, the potentiostat acts as a discrete voltage comparator allowing to generate simple potentiometric pH detection with polyaniline or other electro-active working electrode. Due to the finite instrumental resolutions (ADC and DCA) and the actual method, the voltage and current signals will first evolve then oscillate around the actual voltage of the working electrode and null current respectively. At that moment, if a lower resistor value is selected in the multiplexer, in order to maintain the current to voltage converter below saturation, the amplitude ratio and phase difference between the voltage and the current oscillations will be indicative of the impedance of the electrochemical cell. Indeed, a typical EIS (Electrochemical Impedance Spectroscopy) measurement consists in applying a small amplitude voltage oscillation (excitation signal) to the electrochemical cell and measuring the resulting current oscillation (response signal). The cell impedance is the electrochemical characteristic relating the voltage and current signals. The actual method can thus be used to measure the electrochemical potential and the electrochemical impedance characteristics of the cell at once.

Experiments showing the effectiveness of the potentiostat disclosed here above are now described.

The potentiostat is home made and is computer controlled via a National Instrument NIDAQ USB-6009 multipurpose control and acquisition card. The programs are built and compiled with Microsoft VisualBasic 5.0.

Two types of electrochemical cell architectures are tested.

Figure 5:
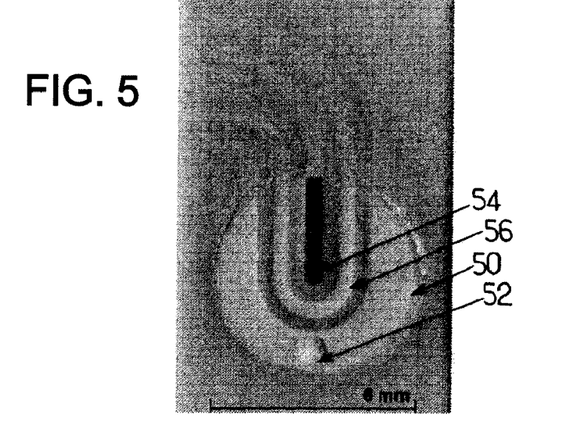
FIG. 5 is a picture of millimetric electrodes used in the system of FIG. 2.

The first type of electrochemical cell is a 200 µL well containing three thin golden film electrodes printed in a circular area of 6 mm diameter, FIG. 5. The platform is a phenolic resin that is commonly used as a substrate for copper printed circuits on board (PCB).

Starting from standard photosensitized copper clad board, these electrodes are obtained by classical printed circuit on board (PCB) realization techniques. As polyaniline cannot be electro-synthesized easily on copper, the copper layer is first etched in the form of a shadow mask for the actual electrode design. The electrode realization is performed with the deposition of a 10 nm titanium layer forming an adherence layer and a 100 nm gold layer obtained by e-beam evaporations. After the e-beam evaporation, the copper mask layer is removed using ferric chloride. All materials and chemicals for PCB realization are purchased from RS components.

The reference electrode 50 is obtained by applying a small spot 52 of solid Ag/AgCl amalgam (Dupont 5874 Silver/Silver Chloride Composition). This solid Ag/AgCl reference electrode has been checked for its stability, repeatability and reliability in different measurement setups from pH 2 to 12. This reference displays an electrode potential 100 mV higher (~300 mV vs. SHE) than a commercial reference electrode (~197 mV vs. SHE).

The polyaniline layer on the working electrode 54 can be obtained by cyclic voltametry or by constant current application. The polyaniline working electrode 54 represented in FIG. 5 was obtained by applying 1.5 µA during 10 minutes in an aqueous solution of 0.2M aniline and 2M HCl using the presented smart sensor architecture. The counter electrode 56 is localized between the working electrode 54 and the reference electrode 50.

Figure 6A:
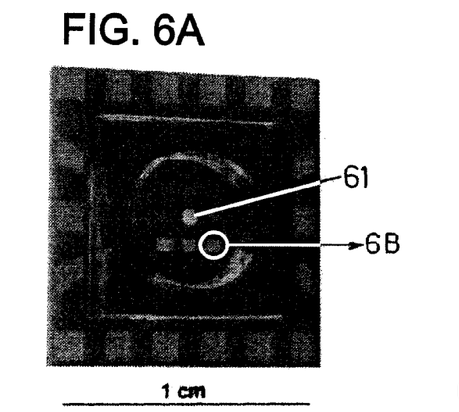
FIG. 6A is a macro picture of the entire chip.
Figure 6B:
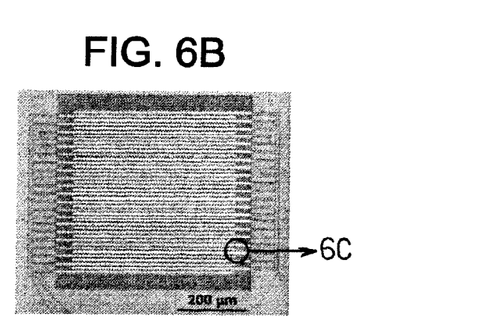
FIG. 6B is an optical microscopy magnification of one set of interdigitated electrodes in which the darker electrode is covered with polyaniline.
Figure 6C:
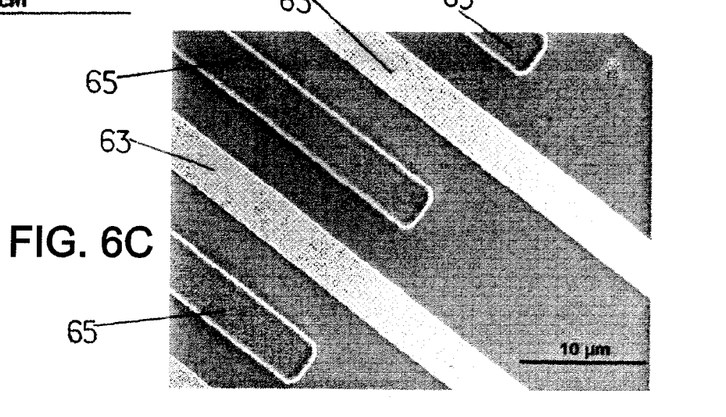
FIG. 6C is a scanning electron microscopy magnification in which the darker electrode is covered with polyaniline.

The second type of electrochemical cell is a 40 µL well containing nine sets of platinum micrometric interdigitated electrodes shown in FIGS. 6A, 6B and 6C. The central set is short-circuited by a small spot 61 of solid Ag/AgCl amalgam (Dupont 5874 Silver/Silver Chloride Composition). This set has been checked as well for its stability and repeatability as a reference electrode in different measurement setups from pH 2 to 12.

The eight remaining sets are used as couples of counter- and working electrodes. The counter electrodes 63 are connected together so that the system contains only one common reference, one common counter and eight individual working electrodes 65.

These platinum electrodes (5 nm Ti, 100 nm Pt) are produced by evaporation and usual photolithography techniques on a 100 nm thick SiO2 layer obtained by dry oxidation of a 360 µm thick silicon substrate. The 6 µm wide electrodes (2*21 digits) are spaced by 6 µm and interdigitated over a square surface of 500*500 µm². For sensing purposes in aqueous solutions, the electrical tracks are insulated from the liquid by means of a 500 nm thick layer of silicon nitride visible in FIGS. 6A and 6B. This layer is obtained by plasma enhanced chemical vapor deposition at 250° C.

The polyaniline layer on the interdigitated working electrodes can be obtained by cyclic voltametry or by constant current application. The polyaniline working electrode visible on FIGS. 6B and 6C is obtained by applying 0.15 µA during 5 minutes in an aqueous solution of 0.2M aniline and 2M HCl using the presented system.

The different pH buffer solutions for pH sensing were obtained using FIXANAL recipes from the Riedel de Haen Company. The conductivity of all these solutions was adjusted at 11 mS using KCl solutions and a Hanna HI255 conductivity meter.

Aniline was distilled twice under argon reduced pressure before use.

All chemicals were purchased from Aldrich Chemicals.

Electrosynthesis and measurements were performed at room temperature.

Classical potentiometry measurements were performed using the millimetric PANI working electrode, a commercial Ag/AgCl reference electrode HI 1083 from Hanna Instruments and a Keithley 2000 voltmeter.

Figure 7A:
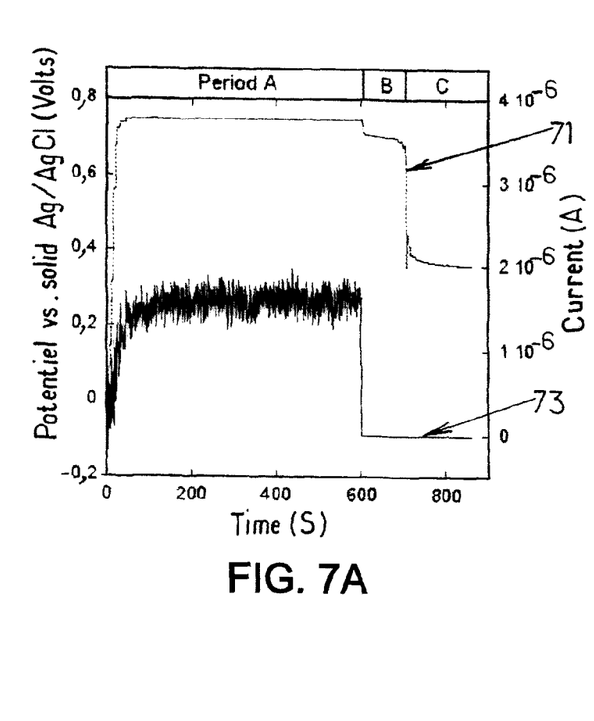
FIG. 7A is a diagram of polyaniline electrosynthesis in period A and subsequent sensing on a millimetric electrode set at periods B and C.
Figure 7B:
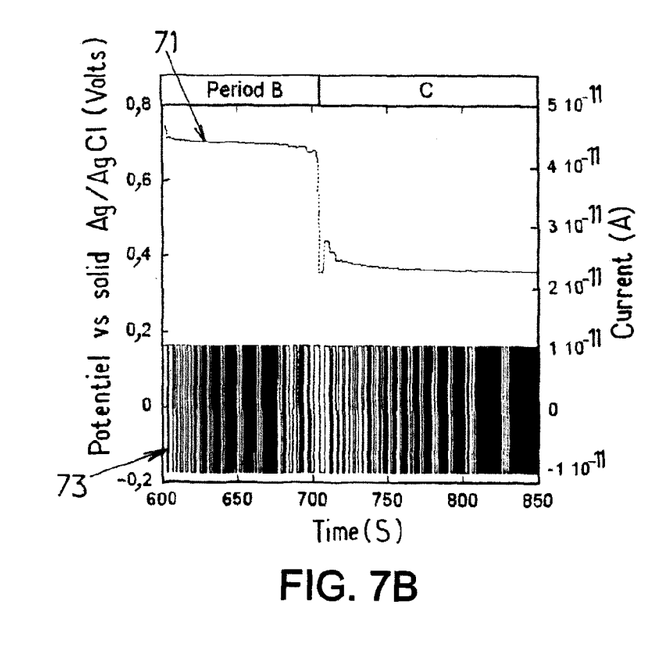
FIG. 7B is magnification of the curve of FIG. 7A for period B and C.

FIG. 7A displays a whole experiment comprising polyaniline electrosynthesis and subsequent sensing on a millimetric electrode setup using the same core algorithm described in relation with FIG. 4 with dS=1 µV and iteration every 100 ms. FIG. 7B is a magnification of Period B, C and of the measured current. The curve 71 shows the input potential with its scale on the left side and curve 73 shows the output current with its scale on the right side.

During period A, polyaniline is electrosynthesized, using the algorithm shown in FIG. 4, maintaining the current of the output signal at a target of 1.5 µA and using a 10 kOhms load resistor in the multiplexer 19. Electrosynthesis occurs at a potential of ~0.75 volts vs. the solid Ag/AgCl reference. After 10 minutes of polyaniline electrosynthesis, period B begins, the load resistor is switched to infinite and the target is set to zero. The PANI working electrode equilibrium potential in its synthesis solution is found at ~0.7 Volts. For period C, the synthesis solution is replaced by a buffer solution at pH 4. The polyaniline working electrode equilibrium potential reaches ~0.37 Volts, indicating the proper functioning of the device as a pH sensor.

The current curve in FIG. 7B clearly illustrates the potentiostat acting as a discrete voltage comparator: as the chosen resistor is infinite, the current passing through the working electrode is limited to the operational amplifier intrinsic current leak. For this reason, the current curved displayed in FIG. 7B is the output of the current to voltage converter (i.e. −5V to 5V) scaled with the operational amplifier intrinsic current leak manufacturer specification (~10 pA). It is interesting to note that this type of signal could directly be used as a binary coded signal for data size reduction. Indeed, as the algorithm is known the potential curve can be reconstructed using this discrete current signal with a simple digital operation.

Figure 3:
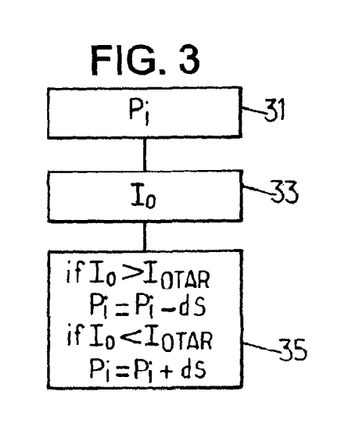
FIG. 3 is a flowchart of a first method of control of the system of FIG. 2.
Figures 8, 9, 10:
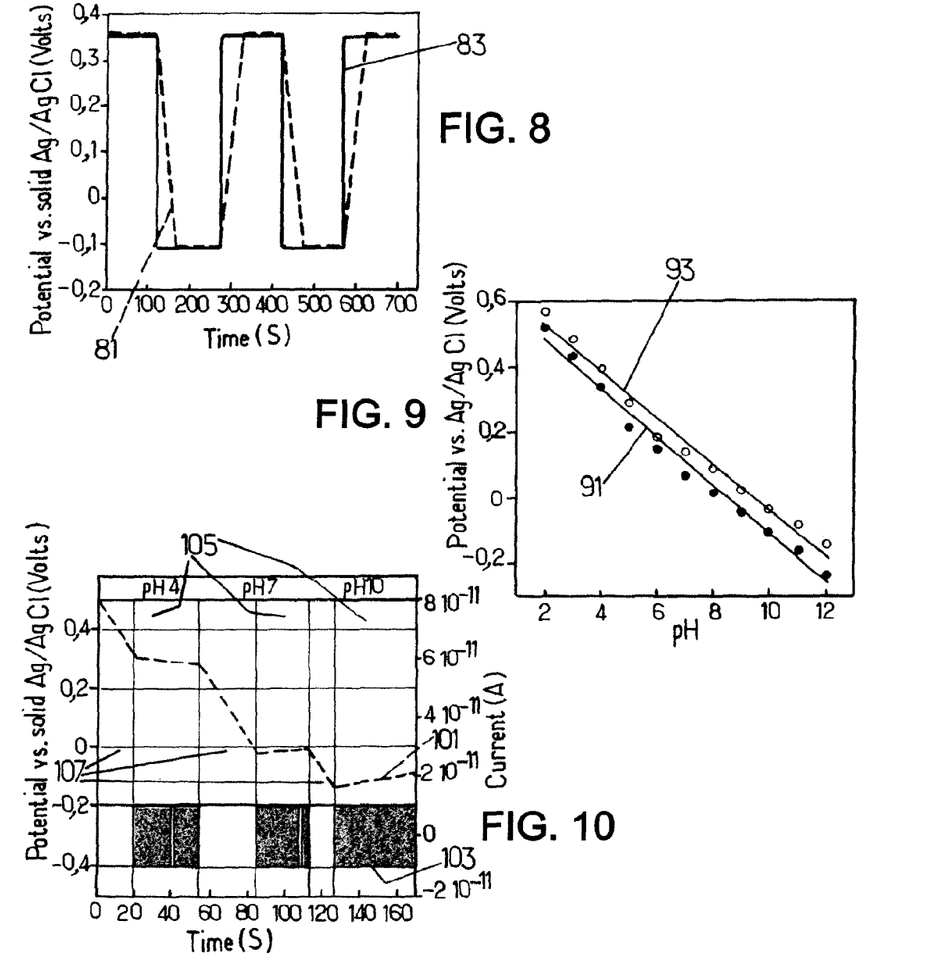
FIG. 8 is a diagram of the potential signal for pH 4 and pH 10 successive detections using the two algorithms of FIGS. 3 and 4 and using the electrode set of FIG. 5.
FIG. 9 is a diagram of the polyaniline potential as a function of pH obtained with the system of FIG. 2 and with a simple voltmeter, a commercial reference electrode and the same working electrode of FIG. 5.
FIG. 10 is a diagram of potential and current signals for pH 4, 7 and 10 detections using the algorithm on FIG. 4.

FIG. 8 illustrates the difference in the measured potential signals 81 and 83 using the algorithms proposed in FIGS. 3 and 4, respectively. The two curves have been obtained by successively switching the buffer solution between pH 4 (~0.36 V) and pH 10 (~−0.1V) with an algorithm iteration every 100 ms, an infinite load resistor and a null target output current. The dashed curve was obtained with a fixed increment and decrement voltage step of dS=1 mV (algorithm of FIG. 3), while the solid curve was obtained with a variable increment and decrement voltage step with dS=1 µV (algorithm of FIG. 4).

From FIG. 8, it is clear that the type of algorithm has its importance in the sensing speed or the time required for the electronic system to reach a quasi equilibrium state. But most importantly this can have a very strong influence if the multiplexer resistor is not infinite and, in fact, in a real instrument, this resistor can never really be infinite.

In FIG. 9, the nernstian response of polyaniline towards pH obtained with the disclosed system, curve 91, is compared to simple voltmeter detection with a commercial reference electrode and the same PANI millimetric electrode, curve 93.

As observed in FIG. 9, the smart sensor and the classical potentiometry experiments display very close slopes of −74 and −70 mV/pH respectively and quite equivalent standard deviations. The observable offset of about 100 mV between the two experiments is only due to the use of different types of Ag/AgCl reference electrodes as explained here above.

The array of micrometric interdigitated electrodes has then been considered. The proximity of the counter electrode to each of the eight working electrodes and their micrometric scale has intuitively been chosen for the confinement of electrical currents into very small separated volumes of the same sample. In this electrochemical cell configuration, classical potentiometry measurements as a function of the pH, using only the working and the solid reference electrodes, have been found difficult to reproduce. The proximity and reduced size of these electrodes is responsible for a constant discharge of the electrochemical cell: the difference in potential between the working and reference electrode tends to cancel as observed in FIG. 10 using the system disclosed here above and one set of micrometric interdigitated electrodes as in FIG. 6A. The current signal rapid oscillations clearly indicate the quasi-equilibrium periods.

The influence of the algorithm could be observed on the cell behavior in the case of micrometric electrodes in which very low current can rapidly change PANI redox states. In FIG. 10, the potential curve 101 of the input signal and the current curve 103 of the current output signal are drawn for three different pH measurements at pH 4, 7 and 10. Each measurement period 105 is preceded by an activation period 107. Algorithm of FIG. 3 was found to produce a reduced noise when compared to algorithm of FIG. 4. From FIG. 10, a simple algorithm could slow down actuation iteration during electronic quasi equilibrium state to maintain the polyaniline charge level more constant.

Figures 11A, 11B:
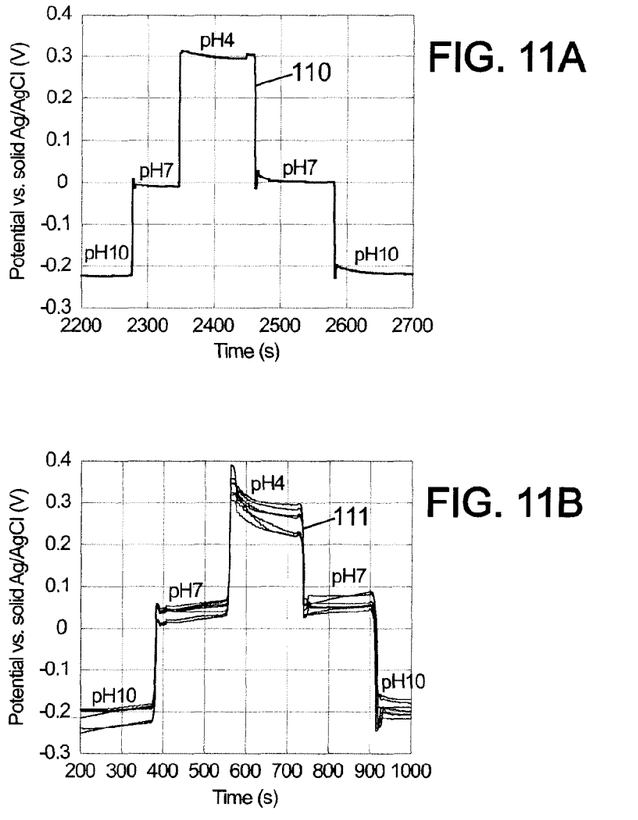
FIG. 11A is a diagram of potential signals for pH 4, 7 and 10 detections using the working electrode of FIG. 5.
FIG. 11B is a diagram of potential signals for pH 4, 7 and 10 detections using the working electrodes of FIG. 6.

However, the algorithm of FIG. 4 allowed to perform faster pH sweeping and thus reduces the effect of constant discharge as observed in FIG. 11A, showing a potential curve 110 for pH 4, 7 and 10 detections using the working electrode of FIG. 5, and in FIG. 11B, showing an array of potential curves 111 for pH 4, 7 and 10 detections using the working electrodes of FIG. 6. Measurements of FIG. 11B also verify reproducibility of eight parallel sensors in an array.

Some little discrepancies can sometimes be observed between pH measurements as when comparing the obtained voltages in FIG. 8 with the ones obtained in FIGS. 11A and 11B. These are the consequence of using Ag/AgCl amalgam as a reference electrode. The amalgam can give small differences in electrochemical potential due to ageing of the used ink. From this observation, it may be useful to calibrate the whole system when measuring the pH in a specific application such as the one that will be described later in FIG. 13.

Figure 12A:
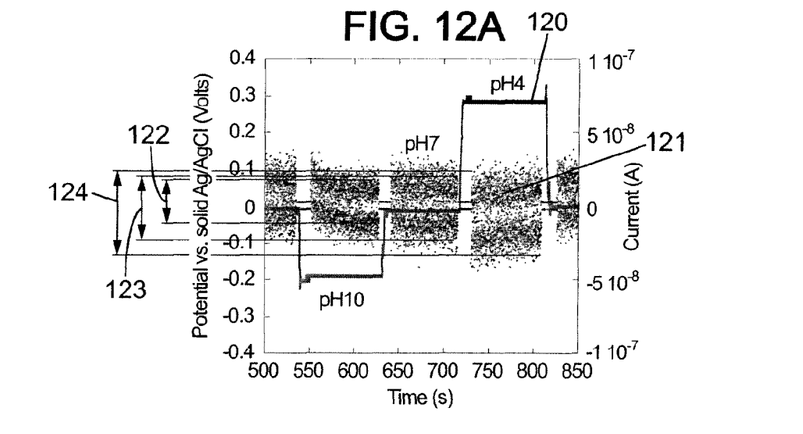
FIG. 12A is a diagram of potential and current signals for pH 4, 7 and 10 detections, showing the influence of the pH on the magnitude of the measured alternating current.

FIG. 12A illustrates the electrochemical potential 120 and the associated current measurements 121 for a polyaniline electrode immersed successively in pH=10, 7 and 4 buffers at 11 mS of conductivity.

During the pH buffer replacements, the current exchanges are deliberately restricted by using an infinite resistor in the current to voltage converter 15 in order to limit redox alterations of the polyaniline. When a stable electrochemical potential is reached, the current exchanges are allowed and measured by using a 1 MOhm resistor in the current to voltage converter 15.

As observed in FIG. 12A, the magnitude of the measured alternating current, resulting from the applied voltage alternations around the actual equilibrium electrochemical potential (observable in FIG. 12B), globally increases when the pH decreases, as it is represented by the arrows 122, 123 and 124, respectively associated to pH=10, pH=7 and pH=4. This observation agrees with the well known polyaniline resistivity increase with pH.

Figure 12B:
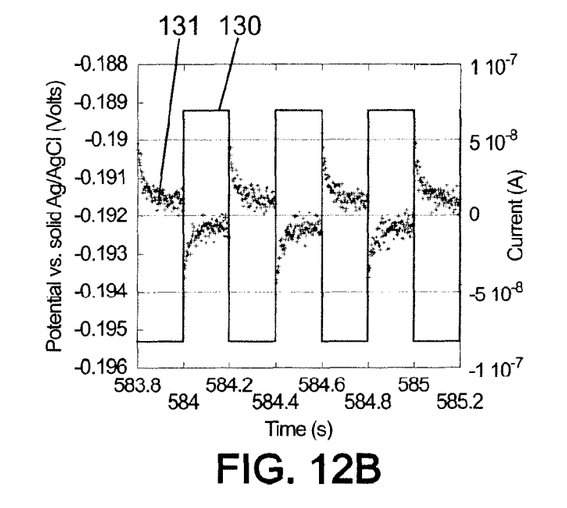
FIG. 12B is an enlargement of the measurements of FIG. 12A at pH=10.

FIG. 12B shows an enlargement of the measurement of FIG. 12A at pH=10. As it can be observed in FIG. 12B, the potential 130 alternates every 200 ms (iteration period) with a chosen amplitude of 6 mV around the equilibrium potential as a consequence of the algorithm. For each iteration, only the first current acquisition is used to apply the algorithm. These square wave low voltage alternations induce successive current relaxations 131. These current relaxation curves 131 are direct indications of electrochemical processes taking place at the working electrode surface (electrochemical impedance, redox processes, etc).

Figure 13:
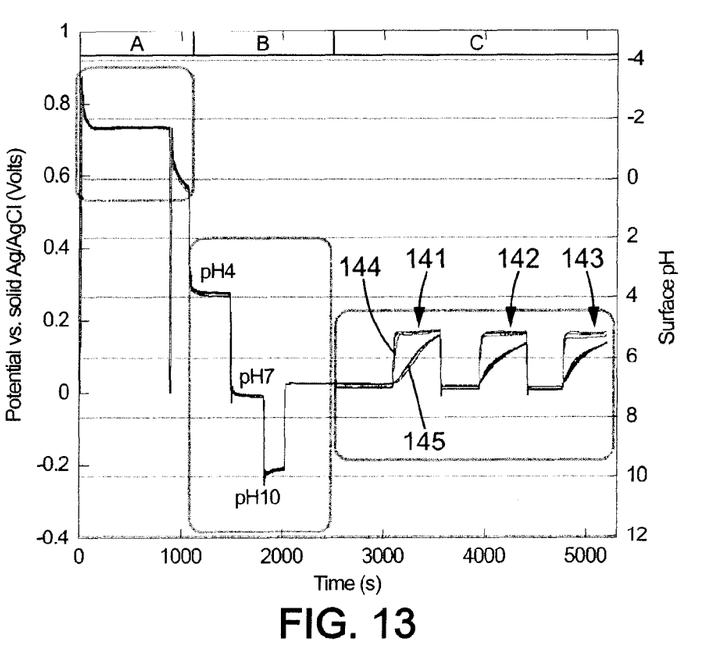
FIG. 13 is a diagram of potential signals detections, showing a variant of realization.

FIG. 13 shows a variant of realization using a β-lactamase enzyme as a sensitizer. β-lactamase enzymes can hydrolyze β-lactam based antibiotics, such as penicillin-G, to lead to a global pH decrease. The experiment starts from eight pristine working electrodes.

During period A, the electrodes are immersed in a 0.2 M aniline, 2 M HCl aqueous solution and polyaniline is electro-synthesized using the algorithm shown in FIG. 4. Electro-synthesis occurs at a potential of about 0.75 volts vs. the solid Ag/AgCl reference. After about 10 minutes of polyaniline electro-synthesis, the load resistor is switched to infinite and the target current is set to zero for all electrodes. The PANI working electrodes equilibrium potentials in their synthesis solution decrease.

During period B, the eight electrodes are successively immersed together in pH=4, 7 and 10 buffers in order to perform a pH calibration used to set the second ordinate axis (pH axis) of FIG. 13.

The measurement is then paused and four of the electrodes are immersed in a 1 μg/ml β-lactamase pH=7 buffer solution while the others are just maintained in a pure pH=7 buffer. After this enzyme adsorption, the eight electrodes are grouped and the measurement is resumed.

During period C, three successive detections 141, 142 and 143 of penicillin G at a 1 mM concentration are done. The electrodes are washed in a pH=7 buffer between each measurement. The four sensitized electrodes display an abrupt response 144 to penicillin, from pH~7 to pH~5, while the other electrodes electrochemical potentials 145 only slowly increase as a consequence of protons diffusion from the sensitized electrodes.

This example demonstrates possible extents of the previous experiments to more specific bio-detection schemes when using enzyme labeled biomarkers.

Very similar results can be obtained on various types of electrodes or working electrode's materials (Au, Pt, Pd, C, inox).

The method may be implemented by a computer program product that is able to implement any of the method steps as described above when loaded and run on computer means. The computer program may be stored/distributed on a suitable medium supplied together with or as a part of other hardware, but may also be distributed in other forms, such as via the Internet or other wired or wireless telecommunication systems.

An integrated circuit may be arranged to perform any of the method steps in accordance with the disclosed embodiments.

While the invention has been illustrated and described in details in the drawings and foregoing description, such illustration and description are to be considered illustrative or exemplary and not restrictive; the invention is not limited to the disclosed embodiment.

Other variations to the disclosed embodiments can be understood and effected by those skilled on the art in practicing the claimed invention, from a study of the drawings, the disclosure and the appended claims. In the claims, the word "comprising" does not exclude other elements and the indefinite article "a" or "an" does not exclude a plurality.

The invention claimed is:

1. A method for measuring a solution pH with a potentiostat, said potentiostat comprising a working electrode made of an electro-conductive solid polymer transducer, an input configured to receive an input signal which provides a working potential to be applied between said working electrode and a reference electrode of the potentiostat, and an output configured to transmit an output signal indicative of the magnitude of the current flowing between a counter electrode of the potentiostat and said working electrode, said three electrodes being immerged into said solution, said method comprising:
generating the input signal;
sensing the output signal;
modifying the input signal and said working potential so as to maintain said output signal inside a predetermined range, wherein the input signal potential is representative of the solution pH when said output signal is maintained inside said predetermined range.

2. The method of claim 1, wherein said method is implemented in a computer software product stored on a recording media as a set of instructions configured to enable a computer to practice the method when the computer executes said set of instructions.

3. A system, comprising:
an electrode cell including a working electrode, a reference electrode and a counter electrode, wherein the working electrode is made of an electro-conductive solid polymer transducer;
a first circuit configured to apply a working potential to the electrode cell in response to a control signal;
a second circuit configured to sense a current flowing between the counter electrode and the working electrode when the working electrode, reference electrode and counter electrode are submerged in a solution under test; and
processing circuitry including:
an analog to digital converter coupled to an output of the second circuit and configured to convert the sensed current to a digital current value;
a digital to analog converter coupled to an input of the first circuit and configured to convert a digital signal to said control signal; and
a processor configured to implement a feedback loop responsive to the sensed current which modifies the digital signal and said working potential so as to maintain the digital current value within a range.

4. The system according to claim 3, wherein the working electrode is made of polyaniline or polypyrrole.

5. A system for measuring a solution pH, comprising:
a potentiostat comprising a working electrode made of an electro-conductive solid polymer transducer, an input configured to receive an input signal which provides a working potential to be applied between said working electrode and a reference electrode of the potentiostat, and an output configured to transmit an output signal indicative of the magnitude of the current flowing between a counter electrode of the potentiostat and said working electrode, said three electrodes configured to be immerged into said solution; and a digital processing circuit having a digital to analog converter for generating said input signal and having an analog to digital converter for generating a digital value representative of the output signal;

wherein the digital processing circuit is configured to modify said input signal and said working potential so as to maintain said digital value representative of said output signal inside a predetermined range;

wherein the input signal potential is representative of the solution pH when said output signal is maintained inside said predetermined range.

6. The system according to claim 3, wherein said second circuit comprises:

an operational amplifier having an input connected to said working electrode and an output providing said sensed current; and a feedback resistance coupled between the input and output of the operational amplifier.

7. The system according to claim 6, where said processor is further configured to control selection of a resistance value for said feedback resistance.

8. The system according to claim 7, wherein said resistance value is selected to avoid saturation of the operational amplifier.

9. The system according to claim 3, wherein said range is external to zero such that a redox state of the electro-conductive solid polymer transducer is modified by a current flow.

10. The system according to claim 8, wherein said output of the second circuit oscillates inside a predetermined range set by selection of the resistance value, the amplitude and phase of said output oscillation being indicative of the electrochemical impedance of said electrode cell.

11. The system according to claim 5, wherein said range is centered on zero.

12. The system according to claim 5, wherein the working electrode is made of polyaniline or polypyrrole.

13. The system according to claim 5, wherein said predetermined range is centered on zero.

14. The system according to claim 13, wherein said potentiostat comprises an operational amplifier having an input connected to said working electrode, the operational amplifier output generating said output signal and said operational amplifier being mounted in parallel with a resistance for acting as a current to voltage converter scaled by said resistance, said resistance being high or infinite to limit the current by saturation of the operational amplifier.

15. The system according to claim 14, wherein said resistance is modified in a range avoiding saturation of the operational amplifier and said output signal predetermined range is external to zero such that the redox state of the electro-conductive solid polymer transducer is modified by a current flow.

16. The system according to claim 14, wherein said resistance is modified in a range avoiding saturation of the operational amplifier so that said output signal oscillates inside said predetermined range, the amplitude and phase of said oscillations being indicative of the electrochemical impedance of said electrochemical cell.

17. The system of claim 5, wherein the electro-conductive solid polymer transducer is sensitized by a proton releasing enzyme mediator.

18. The system according to claim 17, wherein the proton releasing enzyme mediator comprises a $\beta$-lactamase enzyme.

* * * * *